US010689587B2

(12) United States Patent
Al-Sayed et al.

(10) Patent No.: US 10,689,587 B2
(45) Date of Patent: Jun. 23, 2020

(54) SYSTEMS AND PROCESSES FOR CONVERSION OF CRUDE OIL

(71) Applicant: Saudi Arabian Oil Company, Dhahran (SA)

(72) Inventors: Essam Al-Sayed, Al-Khobar (SA); Omer Refa Koseoglu, Dhahran (SA); Lianhui Ding, Dhahran (SA); Abdennour Bourane, Dhahran (SA); Alberto Lozano Ballesteros, Dhahran (SA); Furqan Al Jumah, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/944,068

(22) Filed: Apr. 3, 2018

(65) Prior Publication Data
US 2018/0312767 A1 Nov. 1, 2018

Related U.S. Application Data

(60) Provisional application No. 62/490,175, filed on Apr. 26, 2017.

(51) Int. Cl.
*C10G 69/06* (2006.01)
*C07C 4/02* (2006.01)
(Continued)

(52) U.S. Cl.
CPC ............. *C10G 69/06* (2013.01); *C01B 3/36* (2013.01); *C07C 4/025* (2013.01); *C10G 9/36* (2013.01);
(Continued)

(58) Field of Classification Search
CPC .......... C10G 69/06; C10G 9/36; C10G 47/00; C10G 45/00; C10G 47/32; C10G 2400/26;
(Continued)

(56) References Cited

U.S. PATENT DOCUMENTS 2,358,150 A 4/1941 Cooke
3,617,493 A 11/1971 Wirth et al.
(Continued)

FOREIGN PATENT DOCUMENTS

EP 0197289 A2 10/1986
EP 1600491 A1 11/2005
(Continued)

OTHER PUBLICATIONS

U.S. Office Action dated Mar. 12, 2019 pertaining to U.S. Appl. No. 15/480,917, filed Apr. 6, 2017, 46 pgs.
(Continued)

*Primary Examiner* — Randy Boyer
*Assistant Examiner* — Juan C Valencia
(74) *Attorney, Agent, or Firm* — Dinsmore and Shohl, LLP (57) ABSTRACT

According to an embodiment of the present disclosure, petrochemicals may be produced from crude oil by a process which includes passing the crude oil and hydrogen into a hydroprocessing reactor, separating the hydrotreated oil into a lesser boiling point fraction and a greater boiling point fraction, passing the lesser boiling point fraction to a pyrolysis section of a steam cracker to produce a pyrolysis effluent comprising olefins, aromatics, or both, passing the greater boiling point fraction to a gasifier, where the gasifier produces hydrogen, and passing at least a portion of the hydrogen produced by the gasifier to the hydroprocessing reactor.

20 Claims, 4 Drawing Sheets

(51) Int. Cl.
   *C10G 47/32* (2006.01)
   *C10G 9/36* (2006.01)
   *C10G 47/00* (2006.01)
   *C10G 45/00* (2006.01)
   *C01B 3/36* (2006.01)

(52) U.S. Cl.
   CPC ............ *C10G 45/00* (2013.01); *C10G 47/00* (2013.01); *C10G 47/32* (2013.01); *C01B 2203/0216* (2013.01); *C01B 2203/0255* (2013.01); *C01B 2203/0283* (2013.01); *C01B 2203/04* (2013.01); *C01B 2203/065* (2013.01); *C01B 2203/148* (2013.01); *C10G 2300/1048* (2013.01); *C10G 2300/1077* (2013.01); *C10G 2300/202* (2013.01); *C10G 2300/308* (2013.01); *C10G 2400/20* (2013.01); *C10G 2400/26* (2013.01); *C10G 2400/30* (2013.01)

(58) Field of Classification Search
   CPC .... C10G 2300/1048; C10G 2300/1077; C10G 2400/30; C10G 2300/202; C10G 2400/20; C10G 2300/308; C01B 3/36; C01B 2203/148; C01B 2203/065; C01B 2203/04; C01B 2203/0283; C01B 2203/0255; C01B 2203/0216; C07C 4/025
   See application file for complete search history.

(56) References Cited

U.S. PATENT DOCUMENTS

| | | |
|---|---|---|
| 3,730,879 A | 5/1973 | Christman et al. |
| 3,755,143 A | 8/1973 | Hosoi et al. |
| 3,830,720 A | 8/1974 | Misaki T et al. |
| 3,856,659 A | 12/1974 | Owen |
| 3,862,838 A | 1/1975 | Sloboda |
| 3,862,898 A | 1/1975 | Boyd et al. |
| 3,876,523 A | 4/1975 | Rosinski |
| 4,016,067 A | 4/1977 | Fischer et al. |
| 4,133,777 A | 1/1979 | Frayer et al. |
| 4,134,824 A | 1/1979 | Kamm et al. |
| 4,153,539 A | 5/1979 | Herrington et al. |
| 4,264,435 A | 4/1981 | Read et al. |
| 4,297,203 A | 10/1981 | Ford et al. |
| 4,436,706 A * | 3/1984 | Nacken ............... C01G 31/00 423/594.17 |
| 4,527,003 A | 7/1985 | Okamoto et al. |
| 4,587,011 A | 5/1986 | Okamoto et al. |
| 4,655,904 A | 4/1987 | Okamoto et al. |
| 4,725,349 A | 2/1988 | Okamoto et al. |
| 4,830,728 A | 5/1989 | Herbst et al. |
| 4,992,160 A | 2/1991 | Long et al. |
| 5,019,240 A | 5/1991 | Best et al. |
| 5,171,331 A | 12/1992 | Debras et al. |
| 5,233,121 A | 8/1993 | Modica |
| 5,435,907 A | 7/1995 | Sudhakar et al. |
| 5,523,502 A | 6/1996 | Rubin |
| 5,603,824 A | 2/1997 | Kyan et al. |
| 5,871,650 A | 2/1999 | Lai et al. |
| 5,904,837 A | 5/1999 | Fujiyama |
| 5,906,728 A | 5/1999 | Iaccino et al. |
| 5,951,850 A | 9/1999 | Ino et al. |
| 5,954,947 A | 9/1999 | Mignard et al. |
| 5,958,365 A * | 9/1999 | Liu ............... C01B 3/36 166/267 |
| 6,033,555 A | 3/2000 | Chen et al. |
| 6,123,830 A | 9/2000 | Gupta et al. |
| 6,190,533 B1 | 2/2001 | Bradow et al. |
| 6,190,538 B1 | 2/2001 | Gosselink et al. |
| 6,210,562 B1 | 4/2001 | Xie et al. |
| 6,316,674 B1 | 11/2001 | Kantam et al. |
| 6,384,285 B1 | 5/2002 | Choudary et al. |
| 6,656,346 B2 | 12/2003 | Ino et al. |
| 6,743,961 B2 | 6/2004 | Powers |
| 6,811,684 B2 | 11/2004 | Mohr et al. |
| 6,979,757 B2 | 12/2005 | Powers |
| 6,982,074 B2 | 1/2006 | Jan et al. |
| 7,019,187 B2 | 3/2006 | Powers |
| 7,094,333 B2 | 8/2006 | Yang et al. |
| 7,374,664 B2 | 5/2008 | Powers |
| 7,396,449 B2 | 7/2008 | Powers |
| 7,404,889 B1 | 7/2008 | Powers |
| 7,419,584 B2 | 9/2008 | Stell et al. |
| 7,550,642 B2 | 6/2009 | Powers |
| 7,744,747 B2 | 6/2010 | Halsey |
| 7,785,563 B2 | 8/2010 | Ryoo et al. |
| 7,858,834 B2 | 12/2010 | Powers |
| 7,972,498 B2 | 7/2011 | Buchanan et al. |
| 8,658,019 B2 * | 2/2014 | Bridges ............... C10G 9/005 208/130 |
| 9,096,806 B2 | 8/2015 | Abba et al. |
| 9,228,139 B2 | 1/2016 | Shafi et al. |
| 9,228,140 B2 | 1/2016 | Abba et al. |
| 9,228,141 B2 | 1/2016 | Sayed et al. |
| 9,255,230 B2 | 2/2016 | Shafi et al. |
| 9,279,088 B2 | 3/2016 | Shafi et al. |
| 9,284,497 B2 | 3/2016 | Bourane et al. |
| 9,284,501 B2 | 3/2016 | Sayed et al. |
| 9,284,502 B2 | 3/2016 | Bourane et al. |
| 9,296,961 B2 | 3/2016 | Shafi et al. |
| 2005/0133405 A1 | 6/2005 | Wellington et al. |
| 2006/0118462 A1 | 6/2006 | Schulze-Trautmann et al. |
| 2006/0207917 A1 | 9/2006 | Domokos et al. |
| 2006/0260981 A1 | 11/2006 | Gosling |
| 2007/0090018 A1 * | 4/2007 | Keusenkothen ....... C10G 9/007 208/106 |
| 2007/0108100 A1 * | 5/2007 | Satchell, Jr. ......... C10G 21/003 208/86 |
| 2007/0209968 A1 | 9/2007 | Euzen |
| 2008/0277314 A1 | 11/2008 | Halsey |
| 2008/0283445 A1 | 11/2008 | Powers |
| 2009/0050523 A1 | 2/2009 | Halsey |
| 2009/0218255 A1 | 9/2009 | Claude et al. |
| 2009/0272674 A1 | 11/2009 | Zheng et al. |
| 2010/0018904 A1 | 1/2010 | Kressmann et al. |
| 2010/0155293 A1 | 6/2010 | Verstraete et al. |
| 2010/0230323 A1 | 9/2010 | Ancheyta Juárez et al. |
| 2011/0083996 A1 | 4/2011 | Shafi et al. |
| 2012/0061294 A1 | 3/2012 | Choi et al. |
| 2012/0279728 A1 | 11/2012 | Northrop et al. |
| 2013/0197285 A1 | 8/2013 | Shafi et al. |
| 2013/0220884 A1 | 8/2013 | Bourane et al. |
| 2013/0248416 A1 | 9/2013 | Shafi et al. |
| 2013/0248417 A1 | 9/2013 | Sayed et al. |
| 2013/0248419 A1 | 9/2013 | Abba et al. |
| 2013/0292299 A1 | 11/2013 | Koseoglu et al. |
| 2014/0221712 A1 | 8/2014 | Greene et al. |
| 2015/0001130 A1 | 1/2015 | Akhras et al. |
| 2016/0369185 A1 | 12/2016 | Ward et al. |
| 2018/0147567 A1 | 5/2018 | Matsushita et al. |

FOREIGN PATENT DOCUMENTS

| | | |
|---|---|---|
| GB | 978576 | 12/1964 |
| JP | H06277439 A | 10/1994 |
| WO | 2015000847 A1 | 1/2015 |
| WO | 2015128040 A1 | 9/2015 |
| WO | 2015128041 A1 | 9/2015 |
| WO | 2016059569 A1 | 4/2016 |

OTHER PUBLICATIONS

U.S. Office Action dated Apr. 2, 2019 pertaining to U.S. Appl. No. 15/605,575, filed May 25, 2017, 52 pgs.
International Search Report and Written Opinion pertaining to PCT/US2018/028592 dated Jun. 27, 2018.
Penrose et al., "Enhancing Refinery Profitability by Gasification, Hydroprocessing & Power Generation", Gasification Technologies Conference, Oct. 1999, San Francisco, CA., Texaco Power & Gasification.

(56) References Cited

OTHER PUBLICATIONS

International Search Report and Written Opinion pertaining to International Application No. PCT/US2018/042011 dated Jan. 2, 2019, 20 pages.
International Search Report and Written Opinion pertaining to International Application No. PCT/US2018/042015 dated Jan. 2, 2019, 20 pages.
Examination Report dated Dec. 31, 2018 pertaining to GCC Patent Application No. GC 2017/33492, 6 pages.
Rana et al., "A Review of Recent Advances on Process Technologies for Upgrading of Heavy Oils and Residua", Fuel, 2007, 86, 1216-1231.
International Search Report and Written Opinion pertaining to PCT/US2018/042016 dated Oct. 8, 2018.
International Search Report and Written Opinion pertaining to PCT/US2018/042020 dated Oct. 8, 2018.
Baric, John, "Next-Level Hydrocracker Flexibility: Unlocking High Performance in Today's Turbulent Markets", Shell Global Solutions, 2016, 3-18.
Ding et al., "LCO Hydrotreating with Mo-Ni and W-Ni Supported on Nano- and Micro-Sized Zeolite Beta", Applied Catalysis A: General, 2009, 353 17-23.
Garcia-Martinez et al., "Mesostructured Zeolite Y-High Hydrothermal Stability and Superior FCC Catalytic Performance", Catal. Sci. Technol., 2012, 2, 987-994.
International Search Report and Written Opinion pertaining to PCT/US2017/026498 dated Jun. 30, 2017.
International Search Report and Written Opinion pertaining to PCT/US2017/035202 dated Aug. 7, 2017.
International Search Report and Written Opinion pertaining to PCT/US2017/048130 dated Oct. 18, 2017.
Liu et al., "Y/MCM-41 Composites Assembled from Nanocrystals", Microporous and Mesoporous Materials, 2013, 181, 116-122.
Varoshiotis, Andy, "Cyprus New Energy Economy Focus Should be in the Petrochemicals", 2015, Linkedin.
Zhang et al., "Preparation and Characterization of Beta/MCM-41 Composite Zeolite with a Stepwise-Distributed Pore Structure", Powder Technology, 2008, 73-78.
Office Action pertaining to U.S. Appl. No. 15/683,071 dated Sep. 6, 2018.
Office Action dated Jul. 30, 2019 pertaining to U.S. Appl. No. 15/480,917, filed Apr. 6, 2017, 30 pgs.
Office Action dated Sep. 17, 2019 pertaining to U.S. Appl. No. 16/036,319, filed Jul. 16, 2018, 49 pgs.
Office Action dated Sep. 13, 2019 pertaining to U.S. Appl. No. 16/036,283, filed Jul. 16, 2018, 50 pgs.
Office Action dated Sep. 12, 2019 pertaining to U.S. Appl. No. 16/036,260, filed Jul. 16, 2018, 48 pgs.
Examination Report dated Apr. 15, 2019 pertaining to GCC Patent Application No. 2017/33195, filed Apr. 11, 2017, 5 pages.
Examination Report dated Apr. 2, 2019 pertaining to GCC Patent Application No. 2017/33492, filed Jun. 1, 2017, 5 pages.
Notice of Allowance and Fee(s) Due dated Nov. 20, 2019 pertaining to U.S. Appl. No. 15/480,917, filed Apr. 6, 2017, 13 pgs.
Office Action dated Nov. 7, 2019 pertaining to U.S. Appl. No. 15/605,575, filed May 25, 2017, 39 pgs.
Examination Report dated Mar. 12, 2019 pertaining to GCC Patent Application No. 2017/33869, filed Aug. 23, 2017, 4 pages.
Office Action dated Mar. 24, 2020 pertaining to U.S. Appl. No. 16/789,879, filed Feb. 13, 2020, 12 pgs.
Pural Catapal High-purity alumina hydrates information sheet, SASOL Performance Chemicals, pp. 1-16, no date available.
Examination Report dated Jan. 29, 2020 which pertains to GCC Patent Application No. 2018/35655, with a filing date of Jul. 17, 2018, 5 pages.
Notice of Allowance dated Feb. 19, 2020, pertaining U.S. Appl. No. 16/036,260, 17 pages.
Notice of Allowance dated Feb. 20, 2020, pertaining U.S. Appl. No. 16/036,283, 18 pages.
Notice of Allowance dated Feb. 20, 2020, pertaining U.S. Appl. No. 16/036,319, 18 pages.

\* cited by examiner

SYSTEMS AND PROCESSES FOR CONVERSION OF CRUDE OIL

CROSS-REFERENCE TO RELATED APPLICATIONS

This application claims priority to. U.S. Provisional Patent Application No. 62/490,175 filed Apr. 26, 2017, and entitled "SYSTEMS AND PROCESSES FOR CONVERSION OF CRUDE OIL," which is incorporated by reference herein in its entirety.

TECHNICAL FIELD

Embodiments of the present disclosure relate to systems and processes for producing olefinic and aromatic petrochemicals from crude oil, and are specifically related to systems and processes that utilize hydroprocessing reactors to produce olefinic and aromatic petrochemicals from crude oil.

BACKGROUND

Olefins (e.g., ethylene, propylene, butenes, butadiene) and BTX (benzene, toluene, and xylenes) are basic and essential intermediates of the petrochemical industry. They are mainly produced through thermal cracking (or steam pyrolysis) of petroleum gases and distillates such as naphtha, kerosene or even gas oil. To obtain high yields of olefin and BTX, the preferred feeds for the steam cracker should be highly paraffinic with low aromatic content, because these feedstock properties help reduce undesired products and coke formation.

By upgrading crude oils in a hydroprocessing reactor, the linear paraffinic properties are improved and may be fed directly to a steam cracker, thereby enabling a larger amount of olefins and aromatics to be produced from crude oil directly.

SUMMARY

To ensure the crude oil is converted into a feed having the desired amount of paraffins and minimized amount of aromatics, there are significant hydrogen needs for the hydroprocessing reactor or crude conditioning unit. While the steam cracker unit produces hydrogen that may be recycled to the hydroprocessing reactor, the quantity of recycled hydrogen from the steam cracker is unable to make the system self-sufficient in terms of its hydrogen needs. Accordingly, there is a continual need for self-sufficient systems that produce enough hydrogen for hydroprocessing reactors.

Embodiments of the present disclosure increase hydrogen production for hydroprocessing reactors by gasification of undesirable crude fractions to produce hydrogen. In crude oil conversion processes, about 10 to 15 weight (wt) % of low value, high boiling point (for example, 540° C. and higher) fractions (hereafter called "greater boiling point fraction") has to be rejected to reduce the coke formation within the steam cracker. Embodiments of the present disclosure use this greater boiling point fraction as a feedstock to a gasification unit to produce more hydrogen and generate power. The hydrogen generated from the gasification unit in addition to the pyrolysis hydrogen enables the present crude oil conversion processes to be self-sufficient in terms of hydrogen needs.

In accordance with one embodiment, petrochemicals may be produced from crude oil by a process which may comprise passing the crude oil and hydrogen into a hydroprocessing reactor, separating the hydrotreated oil into a lesser boiling point fraction and a greater boiling point fraction, passing the lesser boiling point fraction to a pyrolysis section of a steam cracker to produce a pyrolysis effluent comprising olefins, aromatics, or both, and passing the greater boiling point fraction to a gasifier. The gasifier may produce hydrogen, and at least a portion of the hydrogen produced by the gasifier may be passed to the hydroprocessing reactor. The hydroprocessing reactor comprising one or more hydroprocessing catalysts that produce the hydrotreated oil.

In accordance with another embodiment, a process for producing olefinic and aromatic petrochemicals is provided. The process includes mixing hydrogen and crude oil to produce a feed stream comprising hydrogen and crude oil and passing the crude oil and hydrogen mixture to a hydroprocessing reactor operating at a temperature from 300° C. to 450° C. and a hydrogen partial pressure from 30 to 200 bar, the hydroprocessing reactor comprising hydroprocessing catalysts that produce a hydrotreated mixture from the crude oil and hydrogen mixture. The hydrotreated mixture is passed to at least one steam cracker comprising a convection section operating at a temperature from 700° C. to 900° C. to produce a heated hydrotreated mixture, which is separated into a lesser boiling point fraction and a greater boiling point fraction. The lesser boiling point fraction is passed to a pyrolysis section of the steam cracker downstream of the convection section to produce a pyrolysis effluent comprising olefins and aromatics and the pyrolysis effluent is transported to at least one separator, where the separator converts the pyrolysis effluent into one or more product streams comprising olefins, aromatics, or combinations thereof. The greater boiling point fraction is passed to a gasifier operating at temperatures of at least 900° C., where the gasifier produces hydrogen, and the hydrogen produced in the gasifier is recycled for mixing with the crude oil upstream of the hydroprocessing reactor.

Additional features and advantages of the embodiments will be set forth in the detailed description which follows, and in part will be readily apparent to those skilled in the art or recognized by practicing the embodiments described in the instant application, including the detailed description which follows, the claims, as well as the appended drawings.

For the purpose of describing the simplified schematic illustrations and descriptions of FIGS. 1-4, the numerous valves, temperature sensors, electronic controllers and the like that may be employed and well known to those of ordinary skill in the art of certain chemical processing operations are not included. Further, accompanying components that are often included in typical chemical processing operations, such as refineries, such as, for example, air supplies, catalyst hoppers, and flue gas handling are not depicted. It should be understood that these components are within the spirit and scope of the present embodiments disclosed. However, operational components, such as those described in the present disclosure, may be added to the embodiments described in this disclosure.

Reference will now be made in greater detail to various embodiments, some embodiments of which are illustrated in the accompanying drawings. Whenever possible, the same reference numerals will be used throughout the drawings to refer to the same or similar parts.

The embodiments set forth in the drawings are illustrative in nature and not intended to be limiting to the claims. Moreover, individual features of the drawings will be more fully apparent and understood in view of the detailed description.

DETAILED DESCRIPTION

As used in the present application, "crude oil" is to be understood to include whole crude oil from conventional sources, as well as crude oil that has undergone some pre-treatment. In some embodiments, "crude oil" can include crude oil from unconventional sources such as fracking light oil and other natural gas condensates. The term "crude oil" is also to be understood to include crude oil that has been subjected to water-oil separation, gas-oil separation, desalting, stabilization, or combinations of such. In certain embodiments, the crude oil stream 5 has an API Gravity (in degrees (°)) of 25° to 50°.

As used in this disclosure, a "reactor" refers to one or more vessels in which one or more chemical reactions may occur between one or more reactants optionally in the presence of one or more catalysts. For example, a reactor may include a tank or tubular reactor configured to operate as a batch reactor, a continuous stirred-tank reactor (CSTR), a plug flow reactor, which will be subsequently described in more detail. Example reactors include packed bed reactors such as fixed bed reactors, and fluidized bed reactors. In embodiments presently described, the hydroprocessing reactor may include multiple reactors in series, such as where a plurality of vessels are connected which each contain a different catalyst.

As used in this disclosure, a "separation unit" or separator refers to any separation device that at least partially separates one or more chemicals that are mixed in a process stream from one another. For example, a separation unit may selectively separate differing chemical species from one another, forming one or more chemical fractions. Examples of separation units include, without limitation, distillation columns, flash drums, knock-out drums, knock-out pots, centrifuges, cyclones, filtration devices, traps, scrubbers, expansion devices, membranes, solvent extraction devices, combinations thereof, and the like. It should be understood that separation processes described in this disclosure may not completely separate all of one chemical constituent from all of another chemical constituent. It should be understood that the separation processes described in this disclosure "at least partially" separate different chemical components from one another, and that even if not explicitly stated, it should be understood that separation may include only partial separation.

Figure 1:
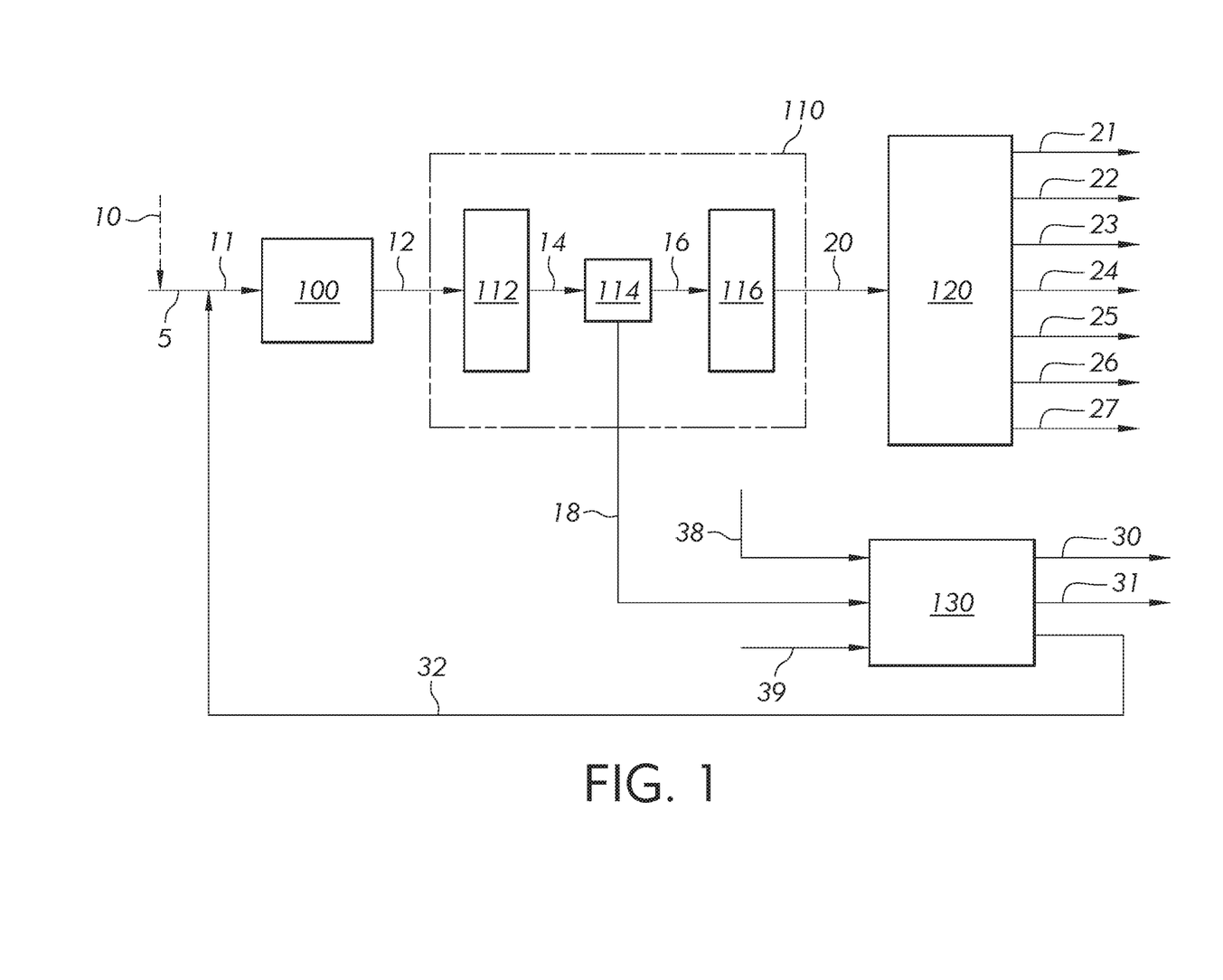
FIG. 1 is a schematic depiction of a crude oil conversion system in accordance with one or more embodiments of the present disclosure.

Referring to the embodiments of FIGS. 1-4, systems and processes for producing olefinic and aromatic petrochemicals from crude oil are depicted. As shown in FIG. 1, the system comprises mixing hydrogen and crude oil to produce a feed stream 11 comprising hydrogen and crude oil. As shown, there may be an optional hydrogen feed 10 provided at the outset of the process for the hydroprocessing reactor 100; however, as will be described subsequently, the present system will generate hydrogen 32 for the hydroprocessing reactor 100.

As would be understood, further optional pretreatment steps are contemplated for the crude oil. For example the crude oil stream 5 can first be optionally passed through a pump (not shown) to create a pressurized crude oil stream before being mixed with hydrogen to produce the feed stream 11 comprising hydrogen and crude oil. In other embodiments, the crude oil stream 5 or pressurized crude oil stream can be passed through a heater (not shown) to create a preheated crude oil stream or preheated or a pressurized crude oil steam, respectively. Thus, in certain embodiments the process includes preheating the crude oil stream 5 to a temperature of at least 300° C. prior to mixing with the hydrogen.

As described infra, the hydrogen can be imported hydrogen, recycled hydrogen from downstream units, or a combination of such. Like the crude oil, the hydrogen mixed with the crude oil can be optionally passed through a heater to create a preheated hydrogen stream or may also be pressurized to produce a preheated and pressurized hydrogen stream, before being mixed with the crude oil, the pressurized crude oil stream, or the preheated and pressurized crude oil steam. In some embodiments, the heater serves to heat the hydrogen stream (or pressurized hydrogen stream) to a temperature of at least 300° C.

Figure 2:
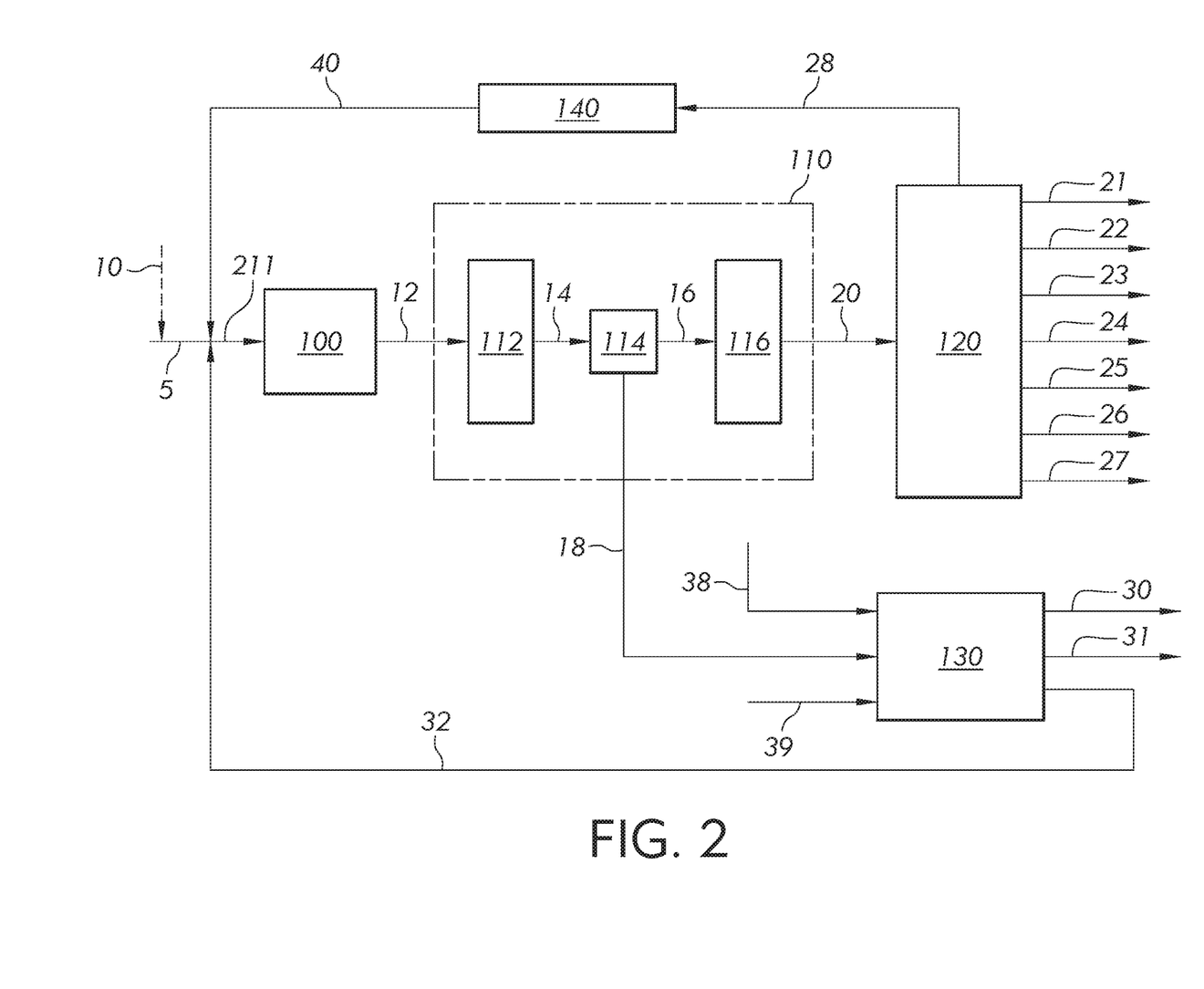
FIG. 2 is another schematic depiction of a crude oil conversion system in accordance with one or more embodiments of the present disclosure.
Figure 3:
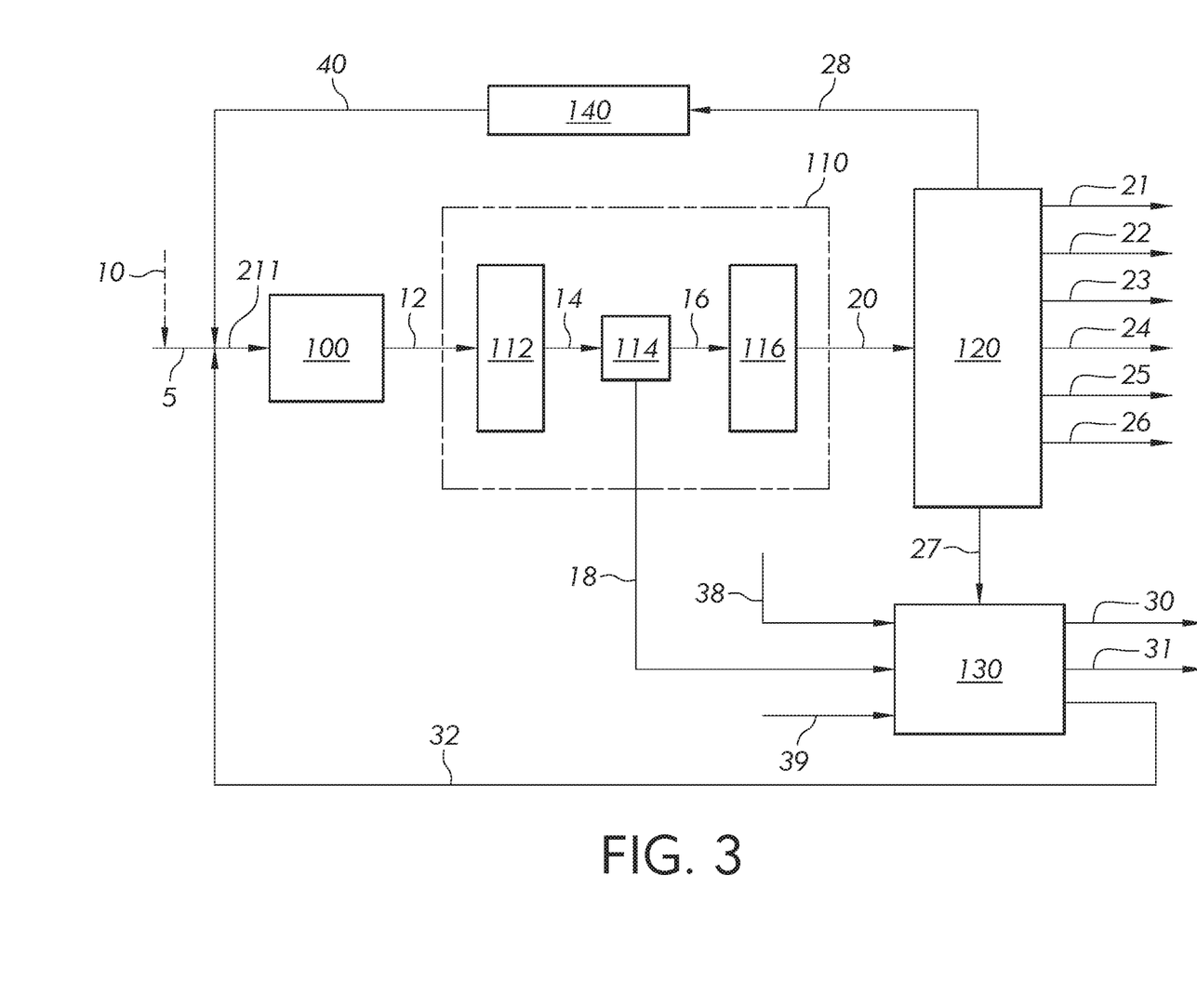
FIG. 3 is yet another schematic depiction of a crude oil conversion system in accordance with one or more embodiments of the present disclosure.
Figure 4:
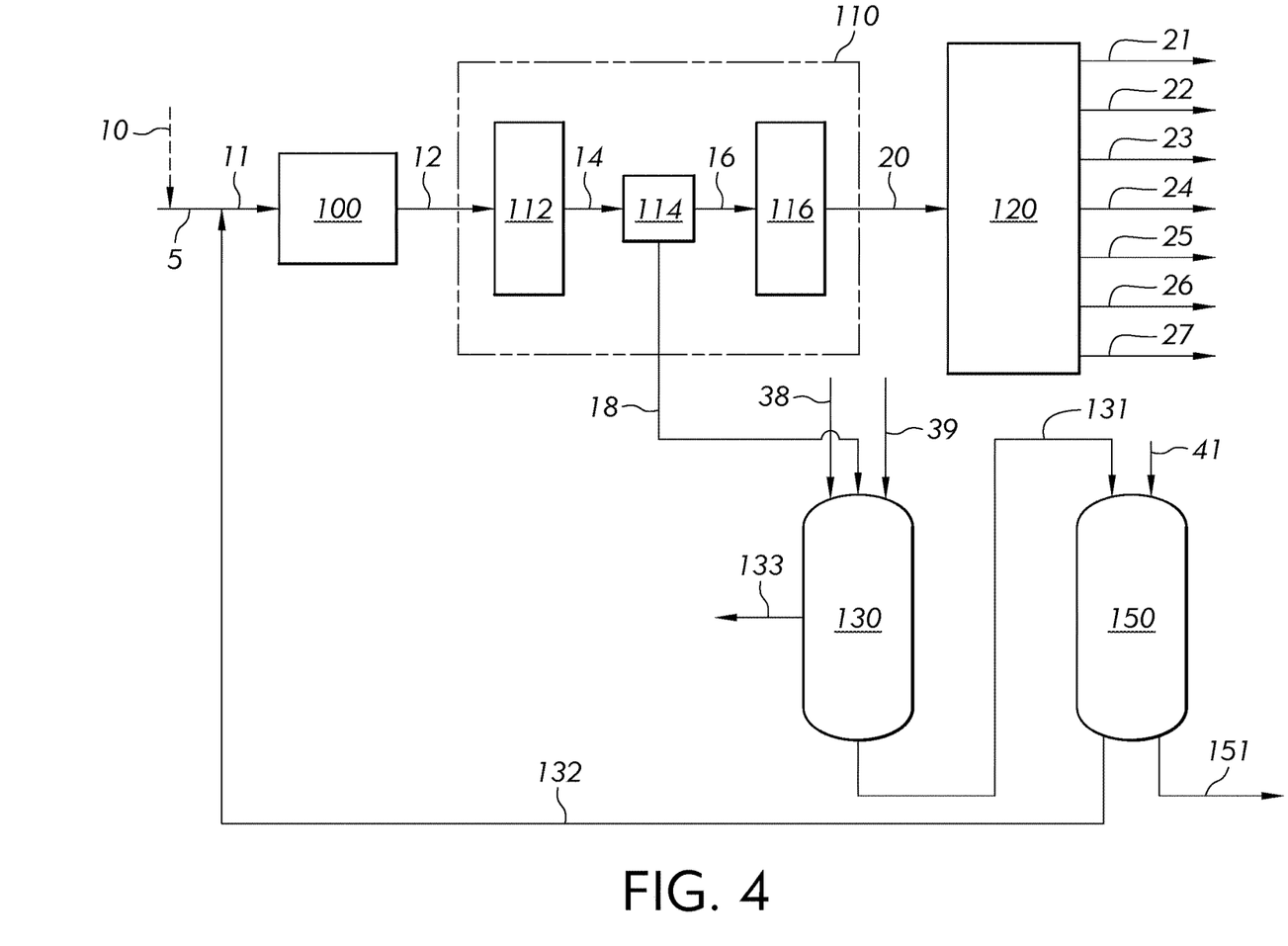
FIG. 4 is another schematic depiction of a crude oil conversion system in accordance with one or more embodiments of the present disclosure.

As shown in FIGS. 1 and 4, the system involves passing the feed stream 11 of crude oil and hydrogen mixture to a hydroprocessing reactor 100 at a temperature from 300° C. to 450° C. and a hydrogen partial pressure from 30 to 200 bar. The hydroprocessing reactor 100, which may also be called a hydrotreater or crude conditioning unit, comprises hydroprocessing catalysts that produce a hydrotreated mixture 12 resulting from hydrotreatment of the feed stream. In FIGS. 2 and 3, the feed stream 211 may include additional sources of hydrogen 32, as will be subsequently described.

In one embodiment, the hydroprocessing reactor 100 includes one or a plurality of beds of hydroprocessing catalysts. The hydroprocessing reactor 100 is able to saturate and convert aromatics, especially polyaromatics to paraffins and naphthenes. Meanwhile, hydroprocessing can also remove majority of the impurities in the oils such as metals, sulfur and nitrogen. Therefore, by selecting appropriate hydroprocessing catalysts and processes, some crude oils can be purified, and thus be suitable as a steam cracker feedstock. The hydrotreating catalysts may include one or more of hydrodemetallization catalysts, hydrocracking catalysts, hydrodearomatization catalysts, hydrodenitrogenation catalysts, hydrodesulfurization catalysts, or both. In one embodiment, the hydrodemetallization catalysts are disposed in a catalyst bed upstream of other hydroprocessing catalysts. As used in the present application, "hydrotreated mixture" means a hydrogen treated admixture of crude oil and hydrogen which has undergone one or more processes selected from hydrodemetallization, hydrodearomatization, hydrodenitrogenation, and hydrodesulfurization, and a "hydrotreated oil" refers to the crude oil which has been hydrotreated and may be contained in the hydrotreated mixture.

The hydroprocessing reactor 100 may include one reactor or multiple reaction vessels in parallel or series. For example, the hydroprocessing reactor 100 can include a plurality of reaction vessels, each containing an effective amount of one or more catalysts, such as hydrodemetallization catalyst, and hydroprocessing catalysts having hydrodearomatization, hydrodenitrogenation, hydrodesulfurization, hydrocracking functions, or combinations of such. In an alternative embodiment, the hydroprocessing reactor 100 may include one or more separation zones, each containing an effective amount of hydrodemetallization catalyst, and an effective amount of hydroprocessing catalysts having hydrodearomatization, hydrodenitrogenation, hydrodesulfurization, hydrocracking functions, or combinations of such. Alternatively, the hydroprocessing reactor 100 can include one or more catalyst layers containing an effective amount of hydrodemetallization catalyst, and one or more catalyst layers containing an effective amount of additional hydroprocessing catalysts having hydrodearomatization, hydrodenitrogenation, hydrodesulfurization, hydrocracking functions, or combinations of such. In additional embodiments, the hydroprocessing reactor 100 includes a hydrodemetallization catalyst. In other embodiments, the hydrodemetallization catalyst can be included in a separate reaction vessel (not shown), or in a separate separation zone. For example, in certain embodiments, the hydrodemetallization catalyst is included in a separate catalyst layer from other catalyst layers.

In some embodiments, the hydroprocessing reactor 100 may include one or more hydrogen quenches, as known to those of skill in the art. The one or more hydrogen quenches are used to control the reaction temperature in the hydroprocessing reactor 100, and are achieved by introducing a hydrogen stream between the one or more reaction vessels, one or more separation zones, or one or more catalyst layers of the hydroprocessing reactor 100. The hydrogen stream used for the hydrogen quenches can be imported hydrogen, recycled hydrogen from downstream units as subsequently described, or a combination of such.

In one particular embodiment, the feed stream 11 passes to a hydroprocessing reactor 100 containing hydrodemetallization catalyst to remove the metals present. Post-demetallization, the feed stream 11 may then be fed to another catalyst bed downstream where additional hydroprocessing catalyst is present with at least 30% extra hydrogen being added for hydrodearomatization, hydrodenitrogenation, hydrodesulfurization, hydrocracking, or all of these. In one or more embodiments, the hydrotreated mixture 12 includes more hydrogen than the feed stream 11.

The hydroprocessing reactor 100 may operate under parameters effective for hydrodemetallization, hydrodearomatization, hydrodenitrogenation, hydrodesulfurization, hydrocracking, or combinations thereof. For example, in some embodiments, the hydroprocessing reactor 100 may operate at a temperature from 300° C. to 450° C. Further temperature ranges include from 300° C. to 330° C., from 300° C. to 350° C., from 320° C. to 360° C., from 340° C. to 380° C., from 360° C. to 400° C., from 380° C. to 420° C., from 400° C. to 430° C., and from 420° C. to 450° C. In some embodiments, the hydroprocessing reactor 100 can operate at a hydrogen partial pressure from 30 to 200 bar. Further hydrogen partial pressure ranges include from 30 to 60 bar, from 30 to 100 bar, from 50 to 100 bar, 75 to 125 bar, 100 to 150 bar, 125 to 175 bar, and 150 to 200 bar. In some embodiments, the liquid hourly space velocity (LHSV) of the hydroprocessing reactor 100 is from 0.1 to 2.0 $h^{-1}$. Further ranges for the LHSV include from 0.1 to 0.5 $h^{-1}$, from 0.5 to 1.0 $h^{-1}$, from 1.0 to 1.5 $h^{-1}$, and from 1.5 to 2.0 $h^{-1}$.

Various compositions are considered suitable for the hydrotreating catalysts. In one or more embodiments, the hydrotreating catalysts comprise at least one metal from Groups 8-10 of the International Union of Pure and Applied Chemistry (IUPAC) Periodic Table, for example, Fe, Co, Ni, or combinations thereof. Moreover, the hydrotreating catalysts may include at least one metal from Group 6 of IUPAC Periodic Table, for example, Mo, W, or combinations thereof. Various support materials are contemplated as suitable. For example, the support may comprise alumina ($Al_2O_3$).

In certain embodiments, the hydrodemetallization catalyst can be supported on a support material. In some embodiments, the support material includes alumina. In certain embodiments, the hydrodemetallization catalyst can include a metal catalyst on a gamma alumina support material, with a surface area of from 140 to 240 square meters per gram ($m^2/g$). Further surface area ranges include from 140 to 160 $m^2/g$, from 160 to 180 $m^2/g$, from 180 to 200 $m^2/g$, from 200 to 220 $m^2/g$, and from 220 to 240 $m^2/g$. This catalyst may have a very high pore volume, for example, in excess of 1 centimeters$^3$/gram ($cm^3/g$). The pore size itself is typically predominantly macroporous, which are pores that are larger than 75 micrometers ($\mu m$). This is to provide a large capacity for the uptake of metals on the catalysts surface and optionally dopants. The active metals on the catalyst surface may comprise sulfides of Ni and Mo in the ratio Ni/Ni+Mo<0.15. The concentration of Ni is lesser on the hydrodemetallization catalyst than other catalysts, as some Ni and vanadium (V) is anticipated to be deposited from the feedstock itself during the removal, acting as catalyst. The dopant used can be one or more of phosphorus (P), boron (B), silicon (Si), and halogens. In certain embodiments, the catalyst can be in the form of alumina extrudates or alumina beads. In other embodiments, alumina beads are used to facilitate un-loading of the catalyst hydrodemetallization layer in the reactor as the metals uptake will range between from 30% to 100% at the top of the layer.

In certain embodiments, the hydroprocessing reactor 100 includes an intermediate catalyst. The intermediate catalyst can also be used to perform a transition between the hydrodemetallization and hydrodesulfurization, or another hydroprocessing function. In some embodiments, the intermediate catalyst can be included in a separate reaction vessel (not shown), or in a separation zone. In some embodiments, the intermediate catalyst is included with the hydrodemetallization catalyst. For example, the intermediate catalyst can be included in the hydrometallization catalyst layer. In some embodiments, the intermediate catalyst is included with the hydrodesulfurization catalyst. For example, the intermediate catalyst can be included in the hydrodesulfurization catalyst layer. In certain embodiments, the intermediate catalyst is included in a separate catalyst layer. For example, the hydrodemetallization catalyst, the intermediate catalyst, and the hydrodesulfurization catalyst are included in separate catalyst layers. In some embodiments, the intermediate catalyst can be supported on a support material, which may include alumina, in one embodiment. The intermediate catalyst can include intermediate metal loadings and pore size distribution. The catalyst can include alumina based support in the form of extrudates, optionally at least one catalytic metal from Group 6 (for example, Mo, W, or combinations of such), or at least one catalytic metals from Groups 8 to 10 (for example, Ni, Co, or combinations of such), or combinations of such. The intermediate catalyst can also contain optionally at least one dopant selected from B, P, Si, and halogens. Physical properties include a surface area of from 140 to 200 m²/g. Further surface area ranges include from 140 to 160 m²/g, from 160 to 180 m²/g, or from 180 to 200 m²/g. Physical properties also include a pore volume of at least 0.6 cm³/g. Physical properties further include pores which are mesoporous and in the range of from 12 to 50 nanometers (nm). Additional ranges include from 12 to 20 nm, from 20 to 30 nm, from 30 to 40 nm, or from 40 to 50 nm.

The hydroprocessing reactor 100 may also include a hydrodesulfurization catalyst. In some embodiments, the hydrodesulfurization catalyst can be included in a separate reaction vessel (not shown), or in a separation zone. For example, the hydrodesulfurization catalyst can be included in a separate catalyst layer from other catalyst layers. In certain embodiments, the hydrodemetallization catalyst, the intermediate catalyst, and the hydrodesulfurization catalyst are included in separate catalyst layers. In certain embodiments, the hydrodemetallization catalyst can be supported on a support material. In some embodiments, the support material includes alumina. In some embodiments, the hydrodesulfurization catalyst can include those having alumina based support materials with a surface area towards the upper end of the hydrodemetallization range, for example, ranging from 180 to 240 m²/g. Additional ranges include from 180 to 195 m²/g, from 195 to 210 m²/g, from 210 to 225 m²/g, or from 225 to 240 m²/g. This required greater surface for hydrodesulfurization results in relatively smaller pore volume, for example, less than 1 cm³/g. The hydrodesulfurization catalyst contains at least one element from Group 6, such as Mo and at least one element from Groups 8 to 10, such as Ni. The catalyst also comprises at least one dopant selected from B, P, Si and halogens. In certain embodiments, cobalt is used to provide relatively increased levels of desulfurization. The metals loading for the active phase is increased as the required activity is greater, such that the molar ratio of Ni/Ni+Mo is in the range of from 0.1 to 0.3 and the (Co+Ni)/Mo molar ratio is in the range of from 0.25 to 0.85.

In certain embodiments, the hydroprocessing reactor 100 can include a catalyst designed to perform hydrogenation of the feedstock (rather than a primary function of hydrodesulfurization). In other embodiments, the catalyst can be included in a separate reaction vessel (not shown), in a separation zone, or in a separate catalyst layer from other catalyst layers. In certain embodiments, the final catalyst can be supported on a support material. In certain embodiments, the support material can include alumina. The final catalyst may be promoted by Ni. Physical properties include a surface area towards the higher end of the range, for example, from 180 to 240 m²/g. Additional ranges include from 180 to 195 m²/g, from 195 to 210 m²/g, from 210 to 225 m²/g, and from 225 to 240 m²/g. This required increased surface to perform hydrogenation results in relatively smaller pore volume, for example, less than 1 cm³/g.

Referring again to FIGS. 1-4, the hydrotreated mixture 12 may then be passed to at least one steam cracker 110 comprising a convection section 112 operating at a temperature from 700° C. to 900° C. to produce a heated hydrotreated mixture 14. Further suitable temperature ranges may include from 700° C. to 750° C., from 750° C. to 800° C., from 800° C. to 850° C., or from 850° C. to 900° C. Steam is also added to the convection section 112 to produce a greater boiling point fraction and a lesser boiling point fraction in the heated hydrotreated mixture 14. Thus, the heated hydrotreated mixture 14 may comprise the greater boiling point fraction and the lesser boiling point fraction for subsequent separation.

In a further embodiment, the steam cracker 110 may comprise a heavy residue rejection section 114 downstream of the convection section 112. The heavy residue rejection section 114 separates the heated hydrotreated mixture 14 into the lesser boiling point fraction 16 and the greater boiling point fraction 18 is contemplated. As shown in FIGS. 1-4, the greater boiling point fraction 18 may be a liquid stream discharged from the bottom of the heavy residue rejection section 114, whereas the lesser boiling point fraction 16 is a vapor stream discharged from a different location on the heavy residue rejection section 114. Any suitable separation vessel which can split the hydrotreated mixture into the lesser boiling point fraction 16 and the greater boiling point fraction 18. This separation may include a flash vessel or any suitable vapor-liquid separator. In some embodiments, gas-liquid separators, oil-liquid separators, fractionators, and the like may be used.

As used in the present application, the greater boiling point fraction is a hydrocarbon containing stream having a boiling point of at least 500° C., and the lesser boiling point fraction is a hydrocarbon containing stream having a boiling point of less than 500° C. In other embodiments, the lesser boiling point fraction is a hydrocarbon containing stream having a boiling point range of less than 540° C., while the greater boiling point fraction is a hydrocarbon containing stream having a boiling point range of higher than 540° C. Characteristics and compositions of the lesser boiling point fraction include a light naphtha fraction, a heavy naphtha fraction, a kerosene fraction, a diesel fraction, and a gas oil fraction boiling between 370° C. and 540° C. Characteristics and compositions of the greater boiling point fraction include a vacuum residue fraction boiling greater than 540° C. Thus, the lesser boiling point fraction includes a higher concentration of "$<C_{40}$ hydrocarbons" (hydrocarbons with less than 40 carbon atoms) than the greater boiling point fraction, while the greater boiling point fraction has a higher concentration of "$>C_{40}$" hydrocarbons (hydrocarbons with greater than 40 carbon atoms) than the lesser boiling point fraction. Additionally, the greater boiling point fraction may include a greater concentration of aromatics than the lesser boiling point fraction.

In some embodiments, the greater boiling point fraction 18 may contain vacuum residue. The greater boiling point fraction 18 may contain solid material. In some embodiments, the greater boiling point fraction 18 may contain an ash-producing component, such as a natural or synthetic oxide. For instance, the greater boiling point fraction 18 may contain natural and synthetic oxides of Si, Al, Fe, Ca, Mg, P, K, Na, S, Ti, or combinations of these. Without being bound by any particular theory, having solids present in the greater boiling point fraction 18 may protect the reactor walls.

While FIGS. 1-4 depict the heavy residue rejection section 114 being used in the separation process, separating the heated hydrotreated mixture 14 into a lesser boiling point fraction and a greater boiling point fraction may be conducted through other mechanisms. For example, the heavy residue section 114 is depicted as being a separate vessel from the convection section 112 in FIGS. 1-4; however, it is contemplated that the convection section 112 may separate the heated hydrotreated mixture 14 into a lesser boiling point fraction and a greater boiling point fraction after preheating the hydrotreated mixture 12.

As shown in FIGS. 1-4, the lesser boiling point fraction 16 is passed to a pyrolysis section 116 downstream of the convection section 112 to produce a pyrolysis effluent 20 comprising olefins and aromatics. The pyrolysis section 116, which is part of the steam cracker 110, operates under parameters effective to crack the lesser boiling point fraction 16 into the pyrolysis effluent 20. The pyrolysis effluent 20 may include olefins (including ethylene, propylene, butenes, and butadiene), aromatics (including benzene, toluene, and xylenes), and pyrolysis gasoline. Also, the pyrolysis section 116 may generate hydrogen, which can be recycled to the hydroprocessing reactor 100.

The processing parameters may be adjusted based on the desired composition pyrolysis effluent. For example, the pyrolysis section 116 may have a steam to light fraction ratio of 0.3:1 to 2:0.1. Moreover, the pyrolysis section 114 may have a reaction residence time of 0.05 to 2 seconds.

Referring again to FIGS. 1-4, the pyrolysis effluent 20 may be fed to at least one separator 120. The separator 120 converts the pyrolysis effluent 20 into one or more product streams comprising olefins, aromatics, or combinations thereof. In some embodiments, the one or more product streams may include BTX (benzene, toluene and xylene) in the pyrolysis fuel oil 27. In the embodiments of FIG. 1, the separator 120 may yield methane 21, ethylene and ethane 22, propene and propane 23, butadiene 24, mixed butenes 25, pyrolysis gasoline 26 and pyrolysis fuel oil 27. In some embodiments, the ethane and propane may be recycled back into the steam cracker 110 and further converted to ethylene and propene.

Additionally, as shown in FIGS. 2 and 3, the separator 120 further produces another hydrogen stream 28 which can be recycled back for mixing with the crude oil 5. In specific embodiments, the hydrogen stream 28 is passed to a hydrogen purification unit 140 to produce a treated hydrogen stream 40. The treated hydrogen stream 40 is then transferred for mixing with the crude oil 5. As shown in the embodiments of FIGS. 2 and 3, the feed stream 211 comprises the treated hydrogen stream 40 and hydrogen 32 from the gasifier 130. These separator product streams are shown for illustration and should not be construed as the only product streams produced in the separator 120.

Various vessels are contemplated for the separator 120. In certain embodiments, the separator 120 may comprises a flash vessel, a fractionator, a distillation vessel or combinations thereof. In some embodiments, the separator 120 can include one or more flash vessels. In certain embodiments, the flash vessel is a flash drum. In some embodiments, the separator 120 can include one or more distillation vessels. The distillation vessel can be a distillation tower, such as a vacuum distillation tower. Moreover, further embodiments of the separator 120 may include gas-liquid separators, oil-liquid separators, or combinations thereof.

Referring again to the system embodiments of FIGS. 1-4, the greater boiling point fraction 18 is fed to a gasifier 130 operating at temperatures of at least 900° C. In one or more embodiments, the gasifier 130 may operate at a temperature of greater than or equal to 900° C., such as from 900° C. to 1700° C., and a hydrogen partial pressure of 20 to 100 bar. Moreover, the gasifier 130 may operate with an oxygen to carbon ratio of 0.3:1 to 10:0.1, and a steam to carbon ratio of 0.1:1 to 10:0.1.

In some embodiments, the gasifier 130 may contain a moving bed system, a fluidized bed system, an entrained-flow systems, or combinations of any of these. The gasifier 130 may include a refractor wall or membrane, which may help insulate the gasifier 130.

The gasifier 130 produces hydrogen 32, which is recycled for mixing with the crude oil 5 upstream of the hydroprocessing reactor 100. Without being bound by theory, this hydrogen 32 from the gasifier 130 helps enable the present system to be self-sufficient in terms of hydrogen needs. As used in the present application, "self-sufficient" means that the present system generates enough hydrogen for the hydroprocessing reactor such that there is not a continual need for fresh hydrogen feed 10. In some embodiments, steam 38 and oxygen 39 may be supplied to the gasifier 130. The gasifier may also produce carbon monoxide 30 and heated streams 31 along with the hydrogen 32.

As shown in FIGS. 2 and 3, the hydrogen needs for the hydroprocessing reactor 100 are supplied by the separator 120 and the gasifier 130, which each produce hydrogen 28, 32 that can be recycled for mixing with the crude oil 5. In some embodiments, hydrogen 28 produced from the separator 120 may be passed to a purification unit 140 for further upgrading and purification steps. The treated hydrogen 40 may then be recycled for use in the feed stream 211. In the embodiment of FIG. 3, the pyrolysis fuel oil 27 produced in the separator 120 may be passed to the gasifier 130, so the gasifier 130 may convert at least a portion of the pyrolysis oil into further hydrogen 32.

Gasification is a process to convert carbonaceous materials to more valuable materials, mainly syngas, by heating it to high temperatures in the presence of steam or a controllable amount of oxygen to facilitate partial oxidation. The term "syngas" refers to synthesis gas, a fuel gas mixture containing mostly hydrogen, carbon monoxide, and some carbon dioxide. The syngas, which may include one or more of hydrogen 32, heat 31, or carbon monoxide 30, then can be further processed to produce pure hydrogen, liquid transportation fuels, or to create electricity.

As shown in FIG. 4, in some embodiments, a water-gas shift reactor 150 may be used downstream of the gasifier for further upgrading. As shown, the gasifier syngas effluent 131, which may include hydrogen, carbon dioxide, and carbon monoxide, may be passed to the water-gas shift reactor 150 along with water 41 to allow for further upgrading, while steam effluent 133 is also discharged from the gasifier 130. The water-gas shift reactor 150 may operate at a temperature of greater than or equal to 150° C., such as from 150° C. to 400° C. The water-gas shift reactor 150 may operate at a hydrogen partial pressure of from 1 to 60 bar. In some embodiments, the water-gas shift reactor 150 may contain a mole ratio of water to carbon monoxide of from 5:1 to 3:1. In other embodiments, the gasifier 130 may contain multiple water-gas shift reactors to convert carbon monoxide to carbon dioxide 151 and additional hydrogen 132, which may be recycled back into the feed stream 11. While depicted as separate streams of carbon dioxide 151 and hydrogen 132 for convenience, it is contemplated that other separation units to separate the syngas components may also be utilized downstream of the water gas shift reactor 150, the gasifier 130, or both.

The features of the present embodiments will be further illustrated in the Examples which follow.

EXAMPLES

Example 1

Example 1 was a pilot plant simulation using SPYRO software. As shown in the following data, the simulation results demonstrated high petrochemical yields and low coke formation from the steam cracking unit when using upgraded Arab Light crude oil as feed.

Table 1 as follows lists properties of Arab light crude oil before being fed to hydroprocessing reactor and after undergoing hydroprocessing in the hydroprocessing reactor. The crude conditioning occurred at a reaction temperature of from 380-400° C. with a liquid hourly space velocity (LHSV) of 0.2-0.5 h$^{-1}$, a hydrogen partial pressure of 150 bar, and an H$^2$/oil ratio of 1200 v/v.

TABLE 1

| Sample | Sulfur wt % | Nitrogen Ppm (wt %) | Total Hydrogen wt % | Density g/mL |
|---|---|---|---|---|
| Arab light | 1.94 | 961 | 12.55 | 0.8584 |
| Upgraded Arab light | 0.01-0.05 | 50-350 | 13.50-14.00 | 0.83-0.84 |

Table 2 lists properties of the rejected greater boiling point fraction after the upgraded Arab light is preheated in the convection section of the steam cracker and separated in the heavy residue rejection section. The steam cracker was operated at a coil out temperature of 840° C. and coil out pressure of 1.8 barg, with a steam to oil ratio (based on weight) of 1:1 and a residence time of 0.2 seconds.

TABLE 2

| Feedstock Composition, wt. % | | | | | | |
|---|---|---|---|---|---|---|
| Carbon | Hydrogen | Nitrogen | Sulfur | Oxygen | Ash | C/H |
| 87.3 | 12.45 | 0.1 | 0.05 | — | — | 7.01 |

Table 3 lists the hydrogen produced when the rejected greater boiling point fraction is fed to the gasifier. 1000 kg of vacuum residue is introduced as a pressurized feedstock into a gasification reactor in the gasification zone (as shown in FIG. 1). Table 1 includes the elemental composition of the vacuum residue feedstock. The gasification reactor is operated at 1045° C. and 30 bar. The ratio of steam-to-carbon is 0.6:1 by weight. The ratio of oxygen-to-carbon is 1:1 by weight. The vacuum residue fraction is partially oxidized to produce hydrogen, carbon monoxide and power. Hydrogen and carbon monoxide are recovered as hot raw synthesis gas and sent to a water-gas shift reaction vessel to increase the hydrogen yield. The water-gas shift reaction is conducted at 318° C. and 1 bar. The mole ratio of steam-to-carbon monoxide is 3:1.

TABLE 3

| | Gasifier, in | Gasifier, out (Kg) |
|---|---|---|
| Feed | 1000 | |
| Oxygen | 1000 | |
| CH$_4$ | | 6.5 |
| H$_2$ | | 271.3 |
| CO | | 92.4 |
| CO$_2$ | | 3153.9 |
| H$_2$O | 2175 | 648.5 |
| Other* | | 2.4 |

*H$_2$S, COS, N$_2$, Ar, NH$_3$

Table 4 lists the petrochemical yield from the separator, which separates the following aromatics and olefins from the pyrolysis effluent. The hydrotreated upgraded product is steam cracked in a pilot plant unit. The liquid oil feed and steam are introduced into the reactor. The reaction conditions are as follows: pressure=1.8 bar, oil/steam ratio=1 kg/kg, reaction temperature 840° C., oil mass flowrate: 3.6 kg/hr. Before the cooling of the cracked effluent, a sample is taken for on-line C5+ analysis by a comprehensive two-dimensional GC (GC×GC). The liquid and tar are separated from the cooler exit by means of a knock-out vessel and a cyclone. A fraction of the product gas is then withdrawn for on-line C4− analysis. The knock out vessel and a cyclone are connected to a container used for collecting pyrolysis fuel oil.

TABLE 4

| Product | Yield, Wt % |
|---|---|
| Hydrogen | 0.6 |
| Methane | 11.5 |
| Ethylene | 25.7 |
| Propylene | 13.3 |
| Butadiene | 5.2 |
| Butenes | 3.6 |
| Benzene | 5.8 |
| Toluene | 3.4 |
| Pyrolysis gasoline | 10.6 |
| Pyrolysis Fuel Oil | 10.1 |
| Fuel Oil | 8.1 |

Example 2

Example 2 includes results of hydroprocessor simulations conducted under different hydroprocessing conditions. The feedstock is listed in Table 5.

TABLE 5

| Density | 0.8607 |
|---|---|
| C, wt % | 85.58 |
| H, wt % | 12.37 |
| S, ppmw | 19810 |
| N, ppmw | 733 |
| Ni, ppm | 4 |
| V, ppm | 15 |
| Narrow fraction yield, wt % | |
| <180° C. | 20.2 |
| 180-350° C. | 30.8 |
| 350-540° C. | 30.3 |
| >540° C. | 18.8 |

Table 6 lists hydroprocessing results under various hydroprocessing conditions.

TABLE 6

| Sample Name | HT-2-380 | HT-2-390 | HT-2-400 | HT-5-380 | HT-5-390 | HT-5-400 |
|---|---|---|---|---|---|---|
| Conditions | | | | | | |
| LHSV, h-1 | | 0.2 | | | 0.5 | |
| Temperature, ° C. | 380 | 390 | 400 | 380 | 390 | 400 |
| Hydrogen partial | 150 | 150 | 150 | 150 | 150 | 150 |

TABLE 6-continued

| Sample Name | HT-2-380 | HT-2-390 | HT-2-400 | HT-5-380 | HT-5-390 | HT-5-400 |
|---|---|---|---|---|---|---|
| pressure, bar | | | | | | |
| $H_2$/oil ratio, v/v | 1200 | 1200 | 1200 | 1200 | 1200 | 1200 |
| Product properties | | | | | | |
| Density | 0.8389 | 0.8306 | 0.8263 | 0.859 | 0.8423 | 0.8391 |
| C, wt % | 86.4 | 85.9 | 86.1 | 86.5 | 86.4 | 86.5 |
| H, wt % | 13.55 | 14.12 | 13.92 | 13.3 | 13.5 | 13.4 |
| S, wppm | 53 | 73 | 57 | 1574 | 764 | 298 |
| N, wppm | 75 | 5 | 80 | 454 | 388 | 169 |
| Ni, ppm | <1 | <1 | <1 | <1 | <1 | <1 |
| V, ppm | <1 | <1 | <1 | <1 | <1 | <1 |
| Product yield, wt % FF | | | | | | |
| $H_2S$ | 2.10 | 2.10 | 2.10 | 1.81 | 1.88 | 1.95 |
| $NH_3$ | 0.08 | 0.09 | 0.08 | 0.03 | 0.07 | 0.07 |
| Methane ($C_1$) | 0.16 | 0.25 | 0.44 | 0.11 | 0.24 | 0.25 |
| Ethene ($C_2$) | 0.16 | 0.27 | 0.43 | 0.10 | 0.24 | 0.30 |
| Propene ($C_3$) | 0.25 | 0.38 | 0.52 | 0.09 | 0.27 | 0.40 |
| Conditions | | | | | | |
| Butene ($nC_4$) | 0.08 | 0.05 | 0.05 | 0.02 | 0.00 | 0.08 |
| Isobutene ($iC_4$) | 0.54 | 0.42 | 0.53 | 0.14 | 0.39 | 0.54 |
| $C_1$-$C_4$ | 1.20 | 1.38 | 1.97 | 0.46 | 1.15 | 1.57 |
| (Pentene) $C_5$-180° C. | 15.82 | 18.62 | 22.07 | 15.51 | 17.00 | 17.62 |
| 180-350° C. | 37.90 | 41.13 | 45.63 | 37.32 | 36.93 | 42.45 |
| 350-540° C. | 31.16 | 30.01 | 22.51 | 31.10 | 30.65 | 28.18 |
| >540° C. | 13.63 | 8.96 | 8.00 | 14.87 | 14.32 | 10.67 |
| $C_5$+ | 98.51 | 98.71 | 98.20 | 98.81 | 98.89 | 98.92 |

The total liquid sample HT-5-390 was fractionated into <540° C. and >540° C. fractions. The <540° C. fraction was named as HT-5-390(<540). The HT-5-390(<540) and HT-2-390 liquid samples were selected for the pilot plant steam cracking test. The result is summarized in Table 7.

TABLE 7

| Feed | HT-2-390 | HT-5-390(<540) |
|---|---|---|
| Operation conditions | | |
| Oil/steam ratio, kg/kg | 1 | 1 |
| Reactor temperature, ° C. | 840 | 840 |
| Reactor pressure, bar | 1.8 | 1.8 |
| Yields, wt % | | |
| $H^2$ | 0.8 | 0.7 |
| Methane | 12.2 | 11.3 |
| Ethane | 3 | 2.7 |
| Ethylene | 25.1 | 23.2 |
| Propane | 0.4 | 0.4 |
| Propene | 12.3 | 11.6 |
| Butane | 0.1 | 0.1 |
| Butene | 3.3 | 3.2 |
| 1,3-C4H6 | 4.5 | 4.6 |
| Benzene | 3.4 | 4.8 |
| Toluene | 1.6 | 4 |
| Xylenes | 0.3 | 1.1 |
| Pyrolysis gasoline | 10.3 | 17.8 |
| Pyrolysis fuel oil | 14.8 | 12.8 |
| Fuel oil | 11.8 | 10.2 |

Example 3

Example 3 relates to the gasification process and again was a pilot plant simulation using an in-house developed software based on large commercial gasification data. For Example 3, 1000 kg of vacuum residue is introduced as a pressurized feedstock into a gasification reactor in the gasification zone (as shown in FIG. 4). Table 8 includes the elemental composition of the vacuum residue feedstock. The gasification reactor is operated at 1045° C. and 30 bar. The ratio of steam-to-carbon is 0.6:1 by weight. The ratio of oxygen-to-carbon is 1:1 by weight. The vacuum residue fraction is partially oxidized to produce hydrogen, carbon monoxide and power. Hydrogen and carbon monoxide are recovered as hot raw synthesis gas and sent to a water-gas shift reaction vessel to increase the hydrogen yield. The water-gas shift reaction is conducted at 318° C. and 1 bar. The mole ratio of steam-to-carbon monoxide is 3:1. The products yield is summarized in Table 9.

TABLE 8

| Vacuum Residue Component | Wt % |
|---|---|
| C | 87.3 |
| H | 12.45 |
| S | 0.05 |
| N | 0.1 |
| O | 0 |
| Ash | 0 |

Table 8 shows the feedstock properties of the vacuum residue fraction that was introduced to the gasification reactor. The molecular weight was estimated at 800 kg/kg-mol.

TABLE 9

| Fraction Components (kg) | Feedstock to Gasifier | Syn Gas from Gasifier to Water-Gas-Shift Reactor | Recovered Product from Water-Gas-Shift Reactor |
|---|---|---|---|
| Pitch | 1000 | | |
| Pitch (HC) | | 998.5 | |
| Oxygen | 1000 | | |
| $CH_4$ | | 6.6 | 6.6 |
| $H_2$ | | 148.4 | 277.7 |
| CO | | 1892.3 | 94.6 |

TABLE 9-continued

| Fraction Components (kg) | Feedstock to Gasifier | Syn Gas from Gasifier to Water-Gas-Shift Reactor | Recovered Product from Water-Gas-Shift Reactor |
|---|---|---|---|
| $CO_2$ | | 403.7 | 3228.7 |
| $H_2O$ | 523.8 | 167.9 | 663.9 |
| $H_2S$ | | 0.5 | 0.5 |
| COS | | 0.1 | 0.1 |
| $N_2$ | | 1.8 | 1.8 |
| Ar | | 0 | 0 |
| $NH_3$ | | 0.1 | 0.1 |

As shown in Table 9, almost 278 kg of hydrogen gas is produced from 1000 kg of vacuum residue following the water-gas shift reaction.

It should be apparent to those skilled in the art that various modifications can be made to the described embodiments without departing from the spirit and scope of the claimed subject matter. Thus, it is intended that the specification cover the modifications and variations of the various described embodiments provided such modifications and variations are within the scope of the appended claims and their equivalents.

According to a first aspect of the present disclosure, process for producing olefinic and aromatic petrochemicals from crude oil, the process may comprise mixing hydrogen and crude oil to produce a feed stream comprising hydrogen and crude oil; passing the crude oil and hydrogen mixture to a hydroprocessing reactor operating at a temperature from 300° C. to 450° C. and a hydrogen partial pressure from 30 to 200 bar, the hydroprocessing reactor comprising hydroprocessing catalysts that produce a hydrotreated mixture from the crude oil and hydrogen mixture; passing the hydrotreated mixture to at least one steam cracker comprising a convection section operating at a temperature from 700° C. to 900° C. to produce a heated hydrotreated mixture; separating the heated hydrotreated mixture into a lesser boiling point fraction and a greater boiling point fraction; passing the lesser boiling point fraction to a pyrolysis section of the steam cracker downstream of the convection section to produce a pyrolysis effluent comprising olefins and aromatics; transporting the pyrolysis effluent to at least one separator, where the separator converts the pyrolysis effluent into one or more product streams comprising olefins, aromatics, or combinations thereof; passing the greater boiling point fraction to a gasifier operating at temperatures of at least 900° C., where the gasifier produces hydrogen; and recycling the hydrogen produced in the gasifier for mixing with the crude oil upstream of the hydroprocessing reactor.

A second aspect of the present disclosure may include the first aspect, where the hydroprocessing catalysts include one or more of hydrodemetallization catalysts, hydroprocessing catalysts, hydrodearomatization catalysts, hydrodenitrogenation catalysts, hydrodesulfurization catalysts, or both.

A third aspect of the present disclosure may include the second aspect, where the hydrodemetallization catalysts are disposed in a catalyst bed upstream of the hydroprocessing catalysts.

A fourth aspect of the present disclosure may include any of the preceding aspects, where the hydroprocessing catalysts may comprise at least one metal from Groups 8-10 of the International Union of Pure and Applied Chemistry (IUPAC) Periodic Table; at least one metal from Group 6 of IUPAC Periodic Table; and at least one support material.

A fifth aspect of the present disclosure may include the fourth aspect, where the hydroprocessing catalysts comprise Fe, Co, Ni, Mo, W, or combinations thereof.

A sixth aspect of the present disclosure may include the fourth aspect, where the hydroprocessing catalysts comprise Mo and W supported on a support material comprising alumina ($Al_2O_3$).

A seventh aspect of the present disclosure may include any of the preceding aspects, where the hydroprocessing catalysts desulfurize and demetallize the crude oil and hydrogen mixture to produce a hydrotreated mixture.

An eighth aspect of the present disclosure may include any of the preceding aspects, further comprising a heavy residue rejection section downstream of the convection section, where the heavy residue rejection section separates the heated hydrotreated mixture into the lesser boiling point fraction and the greater boiling point fraction.

A ninth aspect of the present disclosure may include any of the preceding aspects, where the pyrolysis effluent further comprises hydrogen, and where the hydrogen that is mixed with the feed stream comprises the hydrogen from the pyrolysis effluent.

A tenth aspect of the present disclosure may include any of the preceding aspects, where the aromatics of the cracking effluent comprise one or more of benzene, toluene, and xylene.

An eleventh aspect of the present disclosure may include any of the preceding aspects, where the gasifier operates at a temperature of 900° C. to 1700° C., a hydrogen partial pressure of 20 to 100 bar, or both.

A twelfth aspect of the present disclosure may include any of the preceding aspects, where the gasifier has an oxygen to carbon ratio by volume of 0.3:1 to 10:0.1, a steam to carbon ratio by volume of 0.1:1 to 10:0.1, or both.

A thirteenth aspect of the present disclosure may include any of the preceding aspects, where the gasifier comprises a moving bed system, a fluidized bed system, an entrained-flow system, or combinations thereof.

A fourteenth aspect of the present disclosure may include any of the preceding aspects, where the greater boiling point fraction passed to the gasifier comprises a solid material.

A fifteenth aspect of the present disclosure may include the fourteenth aspect, where the solid material comprises an ash-producing component selected from the group consisting of natural and synthetic oxides of Si, Al, Fe, Ca, Mg, P, K, Na, S, Ti, and combinations thereof.

A sixteenth aspect of the present disclosure may include any of the preceding aspects, further comprising passing hydrogen produced in the separator to a hydrogen purification unit, where the hydrogen purification yields a treated hydrogen stream, and passing the treated hydrogen stream for mixing with the crude oil upstream of the hydroprocessing reactor.

A seventeenth aspect of the present disclosure may include any of the preceding aspects, further comprising gas-liquid separators, oil-liquid separators, fractionators, or combinations thereof.

An eighteenth aspect of the present disclosure may include any of the preceding aspects, further comprising passing pyrolysis oil produced in the separator to the gasifier, where the gasifier converts a portion of the pyrolysis oil into hydrogen.

A nineteenth aspect of the present disclosure may include any of the preceding aspects, where the separator comprises a flash vessel, a distillation vessel, or combinations thereof.

A twentieth aspect of the present disclosure may include any of the preceding aspects, where the crude oil stream has an API Gravity (°) of 10° to 40°.

A twenty-first aspect of the present disclosure may include any of the preceding aspects, further comprising preheating the crude oil to a temperature of at least 300° C. prior to mixing with the hydrogen stream.

A twenty-second aspect of the present disclosure may include any of the preceding aspects, where the greater boiling point fraction comprises vacuum residue.

A twenty-third aspect of the present disclosure may include any of the preceding aspects, where the gasifier produces hydrogen, carbon monoxide, heat, or combinations thereof.

A twenty-fourth aspect of the present disclosure may include the twenty-third aspect, further comprising recovering at least one of the hydrogen or the carbon monoxide as syngas; passing the syngas to a heat exchanger to produce steam and cooled syngas; recovering the cooled syngas; and passing the steam to a turbine to produce electricity.

A twenty-fifth aspect of the present disclosure may include the twenty-fourth aspect, further comprising passing the cooled syngas to a water-gas shift reactor, where the water-gas shift reactor operates at a temperature of from 150° C. to 400° C., a pressure of from 1 to 60 bar, or both.

A twenty-sixth aspect of the present disclosure may include the twenty-fifth aspect, where the water-gas shift reactor comprises a mole ratio of water-to-carbon monoxide of from 5:1 to 3:1.

According to a twenty-seventh aspect of the present disclosure a process for producing petrochemicals from crude oil may include any of the preceding aspects, and may include passing the crude oil and hydrogen into a hydroprocessing reactor, the hydroprocessing reactor comprising one or more hydroprocessing catalysts that produce a hydrotreated oil; separating the hydrotreated oil into a lesser boiling point fraction and a greater boiling point fraction; passing the lesser boiling point fraction to a pyrolysis section of a steam cracker to produce a pyrolysis effluent comprising olefins, aromatics, or both; passing the greater boiling point fraction to a gasifier, where the gasifier produces hydrogen; and passing at least a portion of the hydrogen produced by the gasifier to the hydroprocessing reactor.

A twenty-eighth of the present disclosure may include the first aspect, where the crude oil is combined with the hydrogen to form a mixed stream, which is passed into the hydroprocessing reactor.

A twenty-ninth aspect of the present disclosure may include any of the preceding aspects, where the hydroprocessing reactor operates at a temperature of from 300° C. to 450° C. and a hydrogen partial pressure of from 30 to 200 bar.

A thirtieth aspect of the present disclosure may include any of the preceding aspects, where the process further includes passing the hydrotreated oil to a steam cracker comprising a convection section operating at a temperature of from 700° C. to 900° C. to produce a heated hydrotreated oil.

A thirty-first aspect of the present disclosure may include any of the preceding aspects, where the process further includes transporting the pyrolysis effluent to at least one separator, where the separator converts the pyrolysis effluent into one or more product streams comprising the olefins, aromatics, or both.

A thirty-second aspect of the present disclosure may include any of the preceding aspects, where the gasifier operates at a temperature of at least 900° C.

A thirty-third aspect of the present disclosure may include any of the preceding aspects, where the hydroprocessing reactor comprises one or more of a hydrodemetallization catalyst, hydrocracking catalyst, hydrodearomatization catalyst, hydrodenitrogenation catalyst, or hydrodesulfurization catalyst.

An thirty-fourth aspect of the present disclosure may include any of the preceding aspects, where the hydroprocessing reactor comprises a hydrodemetallization catalyst that is disposed upstream of the other hydroprocessing catalysts.

A thirty-fifth aspect of the present disclosure may include any of the preceding aspects, where the one or more hydroprocessing catalysts reduce the content of sulfur and metals in the crude oil.

A thirty-sixth aspect of the present disclosure may include any of the preceding aspects, where the pyrolysis effluent further comprises hydrogen, which is passed to the hydroprocessing reactor.

A thirty-seventh aspect of the present disclosure may include any of the preceding aspects, where the pyrolysis effluent comprises aromatics selected from one or more of benzene, toluene, or xylene.

A thirty-eighth aspect of the present disclosure may include any of the preceding aspects, where the gasifier comprises a moving bed system, a fluidized bed system, an entrained-flow system, or combinations thereof.

A thirty-ninth aspect of the present disclosure may include any of the preceding aspects, where the greater boiling point fraction comprises a solid material.

A fortieth aspect of the present disclosure may include any of the preceding aspects, where the solid material comprises an ash-producing component selected from the group consisting of natural and synthetic oxides of Si, Al, Fe, Ca, Mg, P, K, Na, S, Ti, or combinations thereof.

A forty-first aspect of the present disclosure may include any of the preceding aspects, where the process further includes passing hydrogen produced in the separator to a hydrogen purification unit, where the hydrogen purification yields a treated hydrogen stream; and passing the treated hydrogen stream for mixing with the crude oil upstream of the hydroprocessing reactor.

A forty-second aspect of the present disclosure may include any of the preceding aspects, where the process further includes passing pyrolysis oil produced in the separator to the gasifier, where the gasifier converts at least a portion of the pyrolysis oil into hydrogen.

A forty-third aspect of the present disclosure may include any of the preceding aspects, where the crude oil stream has an API Gravity of 10 degrees to 40 degrees.

An forty-fourth aspect of the present disclosure may include any of the preceding aspects, further comprising preheating the crude oil to a temperature of at least 300° C. prior to it entering the hydroprocessing reactor.

A forty-fifth aspect of the present disclosure may include any of the preceding aspects, where the greater boiling point fraction comprises vacuum residue.

A forty-sixth aspect of the present disclosure may include any of the preceding aspects, where the gasifier produces hydrogen, carbon monoxide, heated streams, or combinations thereof.

What is claimed is:

1. A process for producing petrochemicals from crude oil, the process comprising:

passing the crude oil and hydrogen into a hydroprocessing reactor, the hydroprocessing reactor comprising one or more hydroprocessing catalysts that produce a hydrotreated oil;

separating the hydrotreated oil into a lesser boiling point fraction and a greater boiling point fraction;

passing the lesser boiling point fraction to a pyrolysis section of a steam cracker to produce a pyrolysis effluent comprising olefins, aromatics, or both;

passing the greater boiling point fraction to a gasifier, where the gasifier produces hydrogen; and passing at least a portion of the hydrogen produced by the gasifier to the hydroprocessing reactor.

2. The process of claim 1, where the crude oil is combined with the hydrogen to form a mixed stream which is passed into the hydroprocessing reactor.

3. The process of claim 1, where the hydroprocessing reactor operates at a temperature of from 300° C. to 450° C. and a hydrogen partial pressure of from 30 to 200 bar.

4. The process of claim 1, further comprising passing the hydrotreated oil to a convection section of the steam cracker operating at a temperature of from 700° C. to 900° C. to produce a heated hydrotreated oil.

5. The process of claim 1, further comprising transporting the pyrolysis effluent to at least one separator, where the at least one separator converts the pyrolysis effluent into one or more product streams comprising the olefins, aromatics, or both.

6. The process of claim 1, where the gasifier operates at a temperature of at least 900° C.

7. The process of claim 1, where the hydroprocessing reactor comprises one or more of a hydrodemetallization catalyst, hydrocracking catalyst, hydrodearomatization catalyst, hydrodenitrogenation catalyst, or hydrodesulfurization catalyst.

8. The process of claim 7, where the hydroprocessing reactor comprises a hydrodemetallization catalyst that is disposed upstream of the other hydroprocessing catalysts.

9. The process of claim 1, where the one or more hydroprocessing catalysts reduce the content of sulfur and metals in the crude oil.

10. The process of claim 1, where the pyrolysis effluent further comprises hydrogen, which is passed to the hydroprocessing reactor.

11. The process of claim 1, where the pyrolysis effluent comprises aromatics selected from one or more of benzene, toluene, or xylene.

12. The process of claim 1, where the gasifier comprises a moving bed system, a fluidized bed system, an entrained-flow system, or combinations thereof.

13. The process of claim 1, where the greater boiling point fraction comprises a solid material.

14. The process of claim 13, where the solid material comprises an ash-producing component selected from the group consisting of natural and synthetic oxides of Si, Al, Fe, Ca, Mg, P, K, Na, S, Ti, or combinations thereof.

15. The process of claim 5, further comprising:

passing hydrogen produced in the separator to a hydrogen purification unit, where the hydrogen purification yields a treated hydrogen stream; and passing the treated hydrogen stream for mixing with the crude oil upstream of the hydroprocessing reactor.

16. The process of claim 5, further comprising passing a pyrolysis fuel oil produced in the separator to the gasifier, where the gasifier converts at least a portion of the pyrolysis fuel oil into hydrogen.

17. The process of claim 1, where the crude oil has an API Gravity of 10 degrees to 40 degrees.

18. The process of claim 1, further comprising preheating the crude oil to a temperature of at least 300° C. prior to it entering the hydroprocessing reactor.

19. The process of claim 1, where the greater boiling point fraction comprises vacuum residue.

20. The process of claim 1, where the gasifier produces hydrogen, carbon monoxide, heated streams, or combinations thereof.

* * * * *